(12) United States Patent
Haberstroh et al.

(10) Patent No.: US 8,563,326 B2
(45) Date of Patent: Oct. 22, 2013

(54) SAMPLE HOLDER AND METHOD OF USING THE SAME

(75) Inventors: Klaus Haberstroh, Bodman-Ludwigshafen (DE); Konrad Faulstich, Stockach (DE)

(73) Assignee: Qiagen Lake Constance GmbH, Stockach (DE)

( * ) Notice: Subject to any disclaimer, the term of this patent is extended or adjusted under 35 U.S.C. 154(b) by 344 days.

(21) Appl. No.: 12/933,832

(22) PCT Filed: Mar. 31, 2009

(86) PCT No.: PCT/EP2009/002333
§ 371 (c)(1),
(2), (4) Date: Dec. 1, 2010

(87) PCT Pub. No.: WO2009/121556
PCT Pub. Date: Oct. 8, 2009

(65) Prior Publication Data
US 2011/0067489 A1    Mar. 24, 2011

(30) Foreign Application Priority Data
Mar. 31, 2008 (EP) .................................. 08006294

(51) Int. Cl.
*G01N 33/53* (2006.01)

(52) U.S. Cl.
USPC ............ 436/180; 436/174; 422/501; 422/500

(58) Field of Classification Search
USPC .......... 435/30, 309.1; 436/174, 180; 422/400, 422/401, 412, 408, 418, 419, 68.1, 500, 422/501; 73/61.55, 61.59, 61.68, 64.56, 73/863, 863.23, 864, 864.51, 864.91
See application file for complete search history.

(56) References Cited

U.S. PATENT DOCUMENTS

| | | | |
|---|---|---|---|
| 4,682,890 A | 7/1987 | DeMacario et al. | |
| 5,284,753 A | * | 2/1994 | Goodwin, Jr. ................. 435/30 |

(Continued)

FOREIGN PATENT DOCUMENTS

| | | |
|---|---|---|
| JP | 6-94731 | 4/1994 |
| JP | 2005-507492 | 3/2005 |

(Continued)

OTHER PUBLICATIONS

International Search Report of PCT/EP2009/002333 dated Jun. 6, 2009.
Written Opinion of PCT/EP2009/002333 dated Jun. 6, 2009.
European Office Action No. 09 727 143.1 dated Nov. 14, 2011.

*Primary Examiner* — Yelena G Gakh
*Assistant Examiner* — Christopher A Hixson
(74) *Attorney, Agent, or Firm* — Baker Donelson Bearman Caldwell & Berkowitz, PC

(57) ABSTRACT

A sample holder, such as a microscope slide, is provided in the form of a card-shaped substrate or plate, preferably for use in an analytical reader. The sample holder comprises at least one hole, preferably a plurality of holes, for receiving a sample to be analyzed. The at least one hole extends completely through the substrate and is sized such that the sample is held within the at least one hole by means of the surface tension of the sample against the force of gravity. Optionally the substrate comprises a first upper substrate and a second lower substrate that together embed a porous membrane. As a further option the sample holder comprises a first cover attached to the top side of the first upper substrate and/or a second cover attached to the bottom side of the second lower substrate. Moreover a method for using such a sample holder in an analytical reader is provided, comprising the steps of: filling the at least one hole of the sample holder with a sample and reagent mixture; inserting the sample holder in the analytical reader; and analyzing the sample and reagent mixture in the at least one hole of the sample holder with the analytical reader.

14 Claims, 5 Drawing Sheets

(56) References Cited

U.S. PATENT DOCUMENTS

| | | |
|---|---|---|
| 5,290,705 A | 3/1994 | Davis |
| 5,314,825 A | 5/1994 | Weyrauch et al. |
| 6,387,331 B1 | 5/2002 | Hunter |
| 2002/0072096 A1 | 6/2002 | O'Keefe et al. |
| 2004/0053422 A1 | 3/2004 | Chan et al. |
| 2004/0191924 A1 | 9/2004 | Hunter et al. |
| 2006/0263872 A1 | 11/2006 | Tsukuda |

FOREIGN PATENT DOCUMENTS

| | | |
|---|---|---|
| JP | 2009-509144 | 3/2009 |
| WO | 0230561 | 4/2002 |
| WO | 02/089982 | 11/2002 |
| WO | 2007/035642 | 3/2007 |

\* cited by examiner

US 8,563,326 B2

SAMPLE HOLDER AND METHOD OF USING THE SAME

CROSS REFERENCE TO RELATED APPLICATIONS

This application is a §371 National Stage Application of PCT/EP2009/002333 filed Mar. 31, 2009, which claims priority to European Application No. 08006294.6 filed Mar. 31, 2008.

TECHNICAL FIELD

The invention relates to a sample holder or sample plate and a method for using the same for analytical tests, such as DNA/RNA quantification, protein quantification and clinical tests. In particular the invention relates to a sample holder for an analytical reader, such as an optical reader or an electrochemical reader, for performing such tests.

BACKGROUND OF THE INVENTION

For analytical tests it is known to apply a plurality of samples, for instance, by means of a pipette onto a flat card-shaped substrate and to analyse the samples on this chard-shaped flat sample holder by means of an analytical reader. Moreover, sample holders for analytical tests are known in the form of microtiter plates or microplates. A microtiter plate a flat plate with multiple "wells" used as small test tubes. A microtiter plate typically has 6, 24, 96, 384 or even 1536 sample wells arranged in a rectangular matrix. Each well of a microtiter plate typically holds somewhere between tens of nanoliters to several milliliters of liquid.

The object of the present invention is to provide for a new sample holder and a method of using such a sample holder.

SUMMARY OF THE INVENTION

According to the present invention a sample holder or sample plate, such as a plastic or glass microscope slide, is provided in the form of a card-shaped substrate with at least one hole, preferably a plurality of holes, for receiving at least one sample to be analyzed. The at least one hole extends completely through the substrate and is sized such that the sample is held within the at least one hole by means of the surface tension of the sample against the force of gravity. In other words, in the case of a preferably circularly shaped hole the diameter thereof is configured such that the sample will stay in the hole due to capillary forces (surface tension) acting between the inner surface of the substrate defining the hole and the sample.

Such a sample holder or sample plate is particularly suited to be used in a method for analyzing sample employing an analytical reader, such as the "ESE-Quant Lateral Flow Reader" available from the company ESE GmbH, Stockach, Germany. Further preferred embodiments of the present invention are defined in the dependent claims and described in more detail below.

DETAILED DESCRIPTION OF THE PREFERRED EMBODIMENTS

Figure 1A:
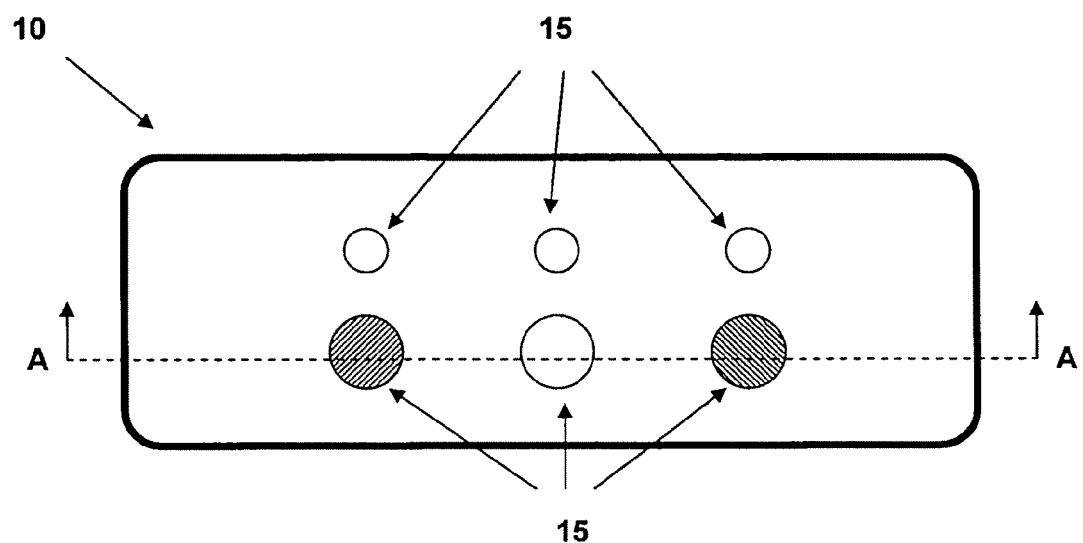
FIG. 1a shows schematically a plan view of an embodiment of a sample holder according to the present invention.

A first embodiment of a sample holder or sample plate according to the present invention is shown in plain view in FIG. 1a. The sample holder 10 is shown to have six holes 15 arranged in an array within the sample holder 10, wherein three of the holes have a diameter which is larger than the diameter of the three other holes. The holes 15 extend completely through the sample holder 10 as can be taken from the cross-sectional view taken along line A-A shown in FIG. 1b. The person skilled in the art will appreciate from the following detailed description that the present invention is not restricted to the number, size, shape and arrangement of holes 15 shown in FIG. 1a. For instance, a sample holder according to the present invention could have less than six holes, such as only one hole, or more than six holes, such as ten holes. In a preferred embodiment all holes 15 have the same diameter and are cylindrical or circular. Preferably, the sample holder 10 has a size similar to a conventional slide for a microscope, e.g. the following dimensions: 7.6 cm (length)×2.6 cm (width)×0.1 cm (height or thickness). It is contemplated that depending on the sample volume to be used larger sample holders can have a thickness of up to 10 cm. However, for most applications the thickness preferably lies in a range between 0.5 and 5 mm. For a given sample volume a larger thickness of the sample holder 10 and smaller hole diameters result in an increased height of the sample to be illuminated. This has the advantage that the analytical reader described below can perform absorption measurements, colorimetric measurements, measurements using reflection and the like. Furthermore, for a given volume an increased height of the sample within a hole leads to less evaporation due to a smaller surface area of the sample.

The sample holder 10 (or more specifically, the substrate thereof) could be made from glass, plastic, metal or the like. Advantageously, the sample holder 10 (or at least certain regions thereof) could be made from a material that can be used as an optical reference or standard material for the measurements performed by means of an optical reader with the sample holder 10 and the samples located in the holes 15 thereof. For instance, the optical properties of the material of the sample holder 10 could be such that the sample holder 10 emits fluorescent light at certain well-defined wavelengths, when illuminated by suitable excitation radiation, and/or absorbs radiation at certain well-defined wavelengths, for instance in the UV and/or visible range. Suitable materials are, for instance, fluorescing minerals, such as ruby, fluorite, turquoise, amber, sapphire, zircon and the like. The person skilled in the art will appreciate that a sample holder 10 (or at least regions thereof) comprising a material having well-defined optical properties that can be used as a reference or standard for an optical reader provides for the advantage that more precise results can be achieved without having to employ an "external" reference, such as a sample standard within one of the holes of the sample holder.

The holes 15 are filled by adding a sample and reagent mixture either sequentially or in one step. The holes 15 are sized such that the respective liquids, i.e. sample and reagent mixture, are held by surface tension and capillary forces therein. As can be taken from the hatched areas in FIG. 1a two of the holes 15 with a large diameter are filled by a mixture of sample and reagent.

The person skilled in the art will appreciate that depending on the physical properties of the sample and reagent mixture to be filled into the holes 15 the diameters of the holes must be small enough so that the surface tension of the sample and reagent mixture will prevent the sample and reagent mixture from falling or dripping out of the hole in the form of a droplet due to gravity. Preferably, the holes have diameters in the range of 0.1-10 mm. Most preferably, in the range of 0.5-3.0 mm.

For some applications it may be advantageous that the inner surfaces of the substrate defining the holes 15 therein can by hydrophilic or hydrophobic surfaces (i.e. more hydrophilic or hydrophobic than the substrate). To this end, these inner surfaces defining the holes 15 could be coated with a layer made from a hydrophilic or a hydrophobic material.

Figure 2A:
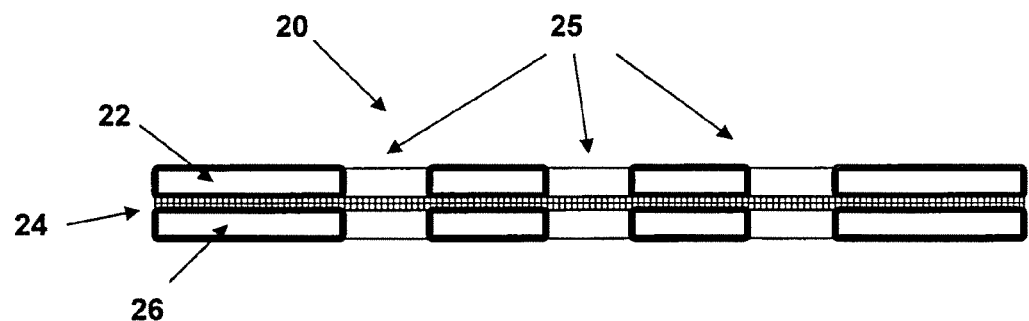
FIG. 2a shows schematically a cross-sectional view of a preferred embodiment of a sample holder according to the present invention.

In another embodiment shown in FIG. 2a, a sample holder 20 essentially consists of three parts in a sandwich-like arrangement, namely a first substrate 22 with holes, a porous membrane 24 and a second substrate 26 with holes. The holes of the first substrate 22 and the holes of the second substrate 26, which correspond in shape, size and arrangement to the holes of the first substrate 22, together define holes 25 extending completely through the substrate (with the porous membrane 24 in between). The porous membrane 24 can serve as a carrier for reagents (e.g. dried down reagents). The porous membrane 24 allows air to vent during the filling process and the liquid to pass from one hole of the first substrate 22 through the porous membrane 24 to the corresponding hole of the second substrate 26. Also the porous membrane 24 can serve as a filter medium (e.g. to filter cells or blood bodies or other components) out of the solution. The porous membrane 24 may also block illumination radiation, such as visible or UV, to reach the hole of the second substrate 26 or may serve to measure migrating particles through the pores in dependence of time and temperature or other parameters. Alternatively or additionally, the membrane could comprise conductive elements, hydrophobic materials or hydrophilic materials. The first 22 and second 26 substrates of the sample holder 20 shown in FIG. 2a are bonded to the porous membrane 24 and are completely separated. The person skilled in the art will, however, appreciate that the first 22 and second 26 substrates also could be formed as unitary piece embedding the porous membrane 24.

Figure 1B:
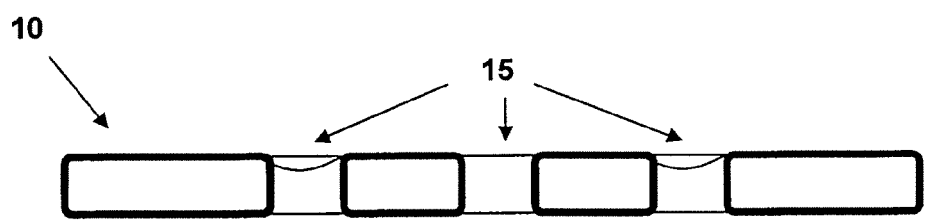
FIG. 1b shows schematically a cross-sectional view of the sample holder of FIG. 1a along the line A-A.
Figure 2B:
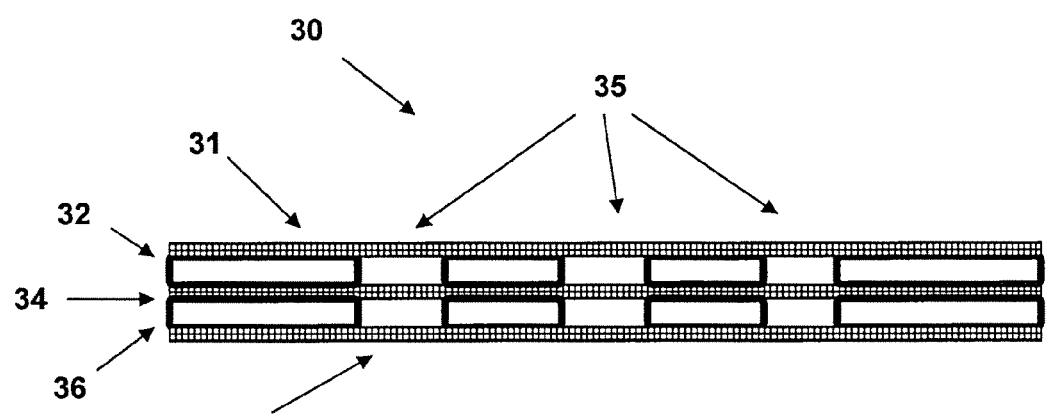
FIG. 2b shows schematically a cross-sectional view of another preferred embodiment of a sample holder according to the present invention.

In a further embodiment of a sample holder 30 shown in FIG. 2b membranes or covers 31, 37 can be used to cover the holes 35 on the top and/or bottom side of the sample holder shown in FIGS. 1b and 2b. These membranes or covers 31, 37 could be transparent for optical, electrochemical or other measurement techniques, and/or could comprise hydrophobic materials or hydrophilic materials.

The holes 15, 25, 35 of the above described sample holders 10, 20, 30 can also be used as reaction vessels, e.g. for nucleic acid amplification and diagnostics tests, ELISA and the like. Instead of manually or robotically filling the holes 15, 25, 35 by means of a pipette, the holes 15, 25, 35 can also be filled by simply immersing the sample holders 10, 20, 30 in a liquid.

Figure 3:
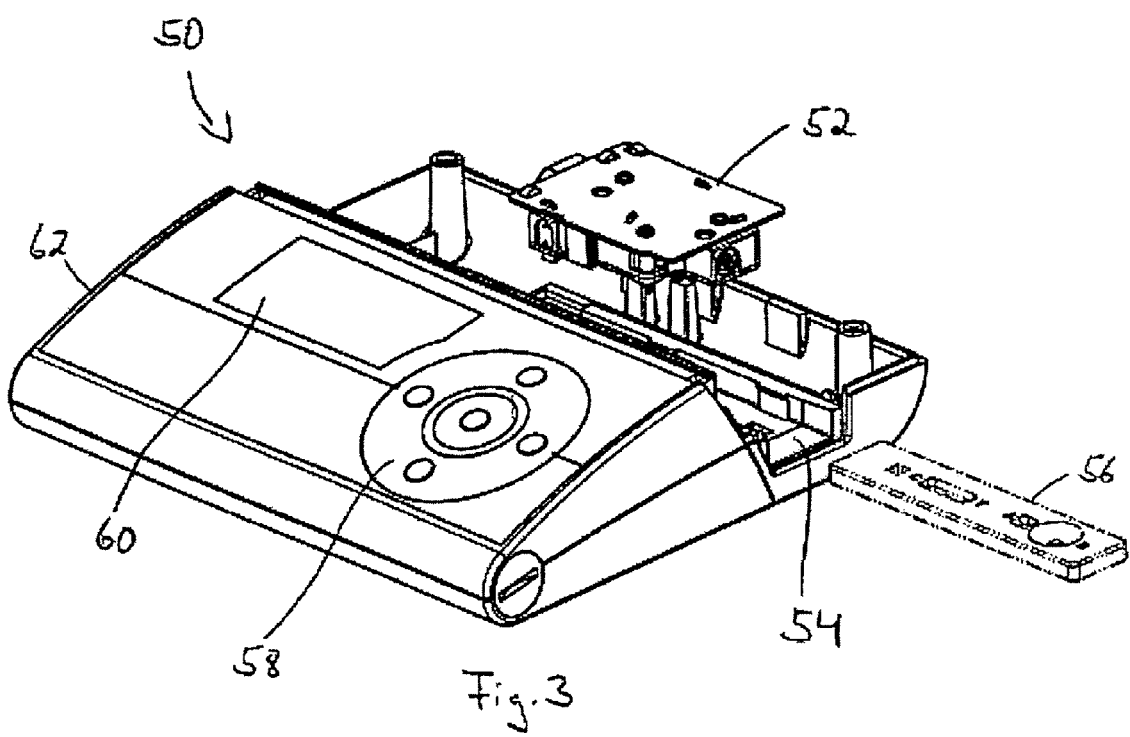
FIG. 3 shows a perspective view of an analytical reader that is particular suited to be used with the sample holders according to the present invention.

The above described sample holders 10, 20, 30 are extremely well suited for the optical measuring device or analytical reader 50 shown in FIG. 3 and described in more detail in the international patent application PCT/EP2008/001468, which hereby is incorporated by reference in its entirety. The measuring device 50 comprises a monolithic electrooptical module 52 comprising the optical and electronic parts for performing a measurement. This module 52, which is described in more detail in the afore-mentioned PCT/EP2008/001468, is designed according to confocal principles rather than an off-axis geometry. The confocal optics of the device makes it unsensitive to mechanical unevenness of a sample and secures highest signal and lowest background intrinsic features of confocal design.

Furthermore, the reader 50 comprises a slot 54 for receiving a sample holder 56 which could correspond to anyone of the above described sample holders 10, 20, 30.

The sample holder 56 can be inserted into the slot 54 and can be moved relatively to the module 52. Additionally, the module 52 can be moved relatively to the sample holder 56.

Moreover, the reader 50 is provided with a key pad 58 for controlling the measurement and a display 60 for showing the obtained results of the measurements.

The reader 50 can measure the color intensity or the fluorescence intensity or chemiluminescence intensity by absorption, reflectrometry, luminometry or fluorescence measurements, or other signals, such as electrochemical signals. The sensor and the sample slide are embedded in the reader, which is a stand alone device including housing, industrial design, electronics, optics, all necessary mechanical parts, display, memory, batteries, connectivity to USB port, printer, barcode reader, and optional wireless data transfer. It has a firmware for device control and data interpretation. Calibration curves can be saved in the internal memory. The reader 50 can be connected and be operated as well through an external computer. The sample holder (slide) can be inserted into the reader by a drawer like carriage and the filling of the holes can occur directly on the sample holder placed in this cartridge. Once the sample holder slides into the reader the reader scans the samples stepwise or on the fly. Results are directly displayed on the display 60 of the reader and/or on an external monitor of a PC connected to the reader 50 for processing and analyzing the results.

It is often desirable to perform a fast quantification of DNA and proteins, such as within a few minutes. Conventional fluorescence tests require 20 minutes or more to obtain a stable signal, because the fluorescence dyes have to bond to the DNA or protein. Furthermore, in the case of small volumes, such as 1 to 2 μl, evaporation cannot be neglected over such time periods. According to the present invention such evaporation can be prevented to negatively affect the tests by adding agents to the sample that inhibit evaporation.

Reagents to minimize or avoid evaporation of sample can be hygroscopic compounds such as, polyethylenglycols, diethylenglycol, glycerin, $MgCl_2$, $LiCl$, $CaCl_2$, $Ca(NO_3)_2$, $ZnCl_2$, and other organic and inorganic compounds such as alcohols and amines and the like.

Additionally or alternatively, the effects of evaporation on the measurements can be taken into account when processing the measured signals. In other words, by using calibrations and/or models for the evaporation and the corresponding signal increase due to a higher concentration of the target within the sample over time the "true" signal can be obtained. To this end calibration curves as a function of time for DNA and protein measurements are necessary. However, the signal also is a function of the added evaporation prohibiting agent as well as the mixing ratio of DNA and protein within in the sample. These mixing ratios are not known and should be determined. To this end calibration curves for known mixing ratios can be used.

Because it is possible to measure more than one sample with the reader simultaneously, the time required for handling the different samples for instance by means of a pipette can delay the measurement such that the signal increases as a function of time. Consequently, the device according to the present invention allows for a determination of that point in time when the first simple is applied (opening the carriage and start of the time measurement). Thereafter the samples (one or more) are applied. Finally the carriage carrying the samples is closed (end of the time measurement). Thus, the total time required for handling of the samples with a pipette can be determined and the time delay can be extrapolated from the first to the last sample. By means of the different calibration curves for different mixing ratios stored within the device a signal correction factor can be determined for each point in time. The results are sufficiently accurate and sensitive for the applications of the reader, such as DNA-protein preparation, forensic applications and the like.

Often the respective samples (plus reagent mixture) will not occupy the whole respective spaces provided by the holes 15, 25, 30. According to the present invention it is possible to determine the volume of the sample and reagent mixture in the holes of the sample holders 10, 20, 30 by means of the reader 50. The liquid (sample plus reagent mixture) in a given hole forms a meniscus, wherein the vertical thickness of the liquid generally is larger towards the walls of the holes than in the middle thereof (due to the capillary forces and the surface tension in this area). The shape of the meniscus (such as determined by the ratio of the peak intensity in the middle of a hole compared to the peak intensity at the wall thereof) can be used to determine the volume of the liquid. The determination of the volume of the sample and reagent mixture of a given hole can be used to take into account the effects of evaporation by determining the surface area of the evaporating liquid (i.e. sample and reagent mixture).

Figure 4A:
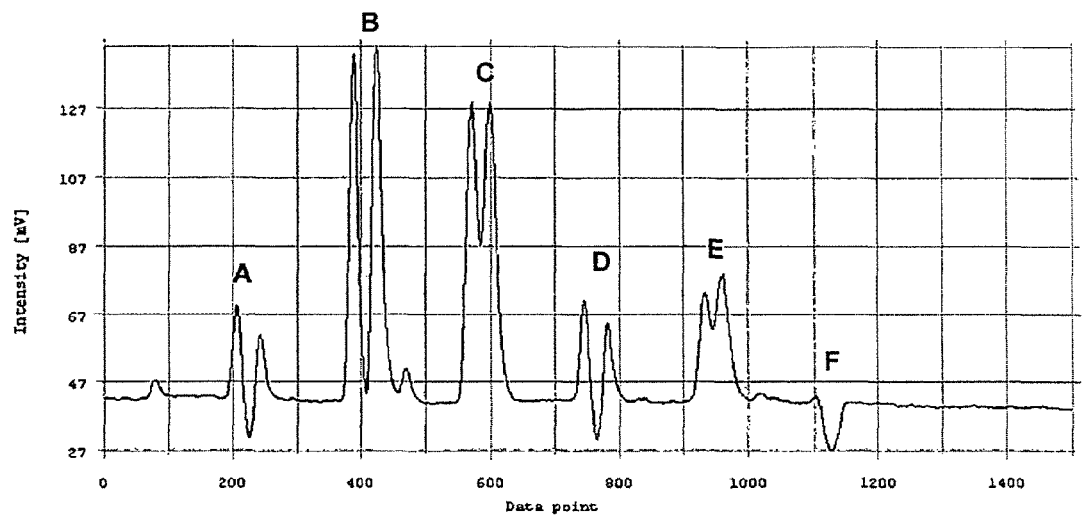
FIGS. 4a to 4d show results obtained with a sample holder according to the present invention and the analytical reader shown in FIG. 3.

FIG. 4a shows exemplary meniscuses measured after 10 min of evaporation for the following example: Protein determination using Fluoroprofile assay (Sigma-Aldrich). Hole diameter: 1 mm, volume: 1 µl; values in µg/ml, sensor focal length: 6 mm, Excitation/Emission 470 nm/625 nm. Meniscus appears as "double peak". The signals at A, B, C, D, E, and F correspond to a blank, 100 µg/ml, 25 µg/ml, 6 µg/ml, 1 µg/ml and an empty hole, respectively. The person skilled in the art will appreciate that in order to resolve the double peak structure caused by a meniscus the resolution of the optical reader has to smaller than the hole diameter.

Figure 4B:
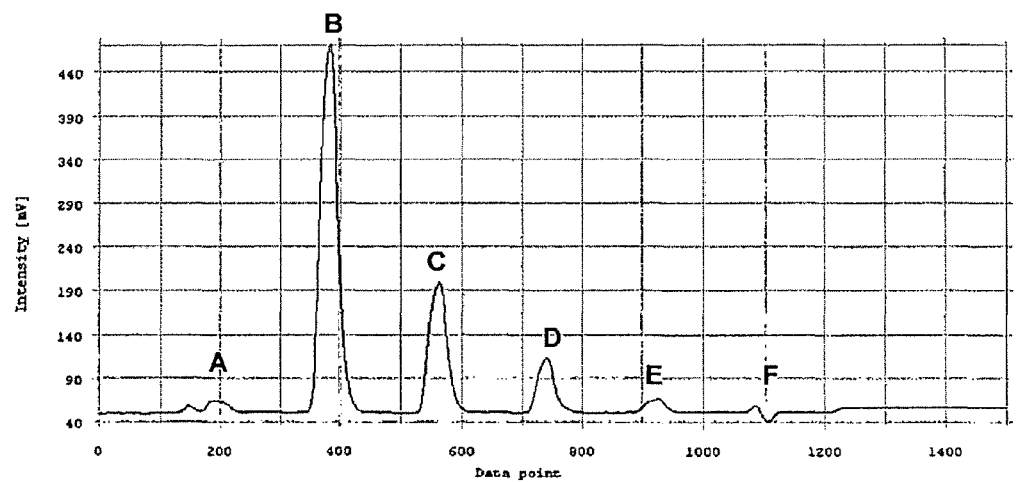

FIG. 4b shows the results of a protein determination using a Fluoroprofile assay (Sigma-Aldrich). Hole diameter: 1 mm, volume: 1 µl; values in µg/ml, sensor focal length: 6 mm, Excitation/Emission 470 nm/625 nm. The signals at A, B, C, D, E, and F correspond to a blank, 100 µg/ml, 25 µg/ml, 6 µg/ml, 1 µg/ml and an empty hole, respectively.

Figure 4C:
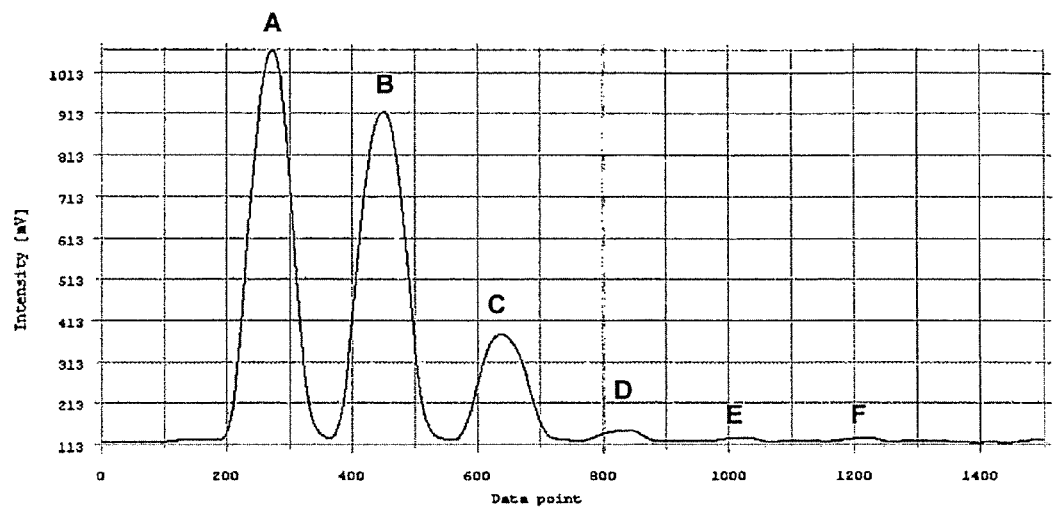
Figure 4D:
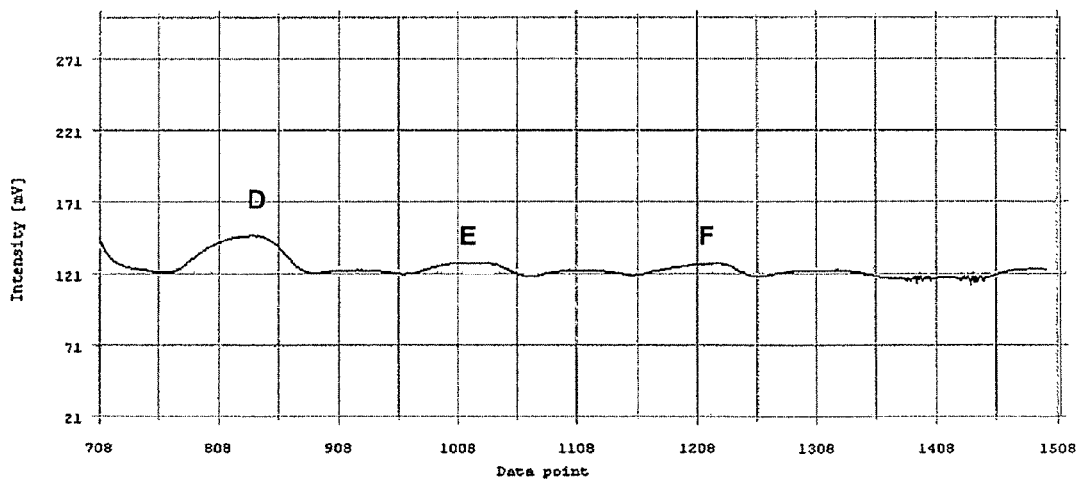

FIG. 4c shows the results of a DNA quantification using Quant-iT PicoGreen ds DNA Assay Kit. Volume 1 µl, sensor focal length: 6 mm, Excitation/Emission 470 nm/520 nm. The signals at A, B, C, D, E, and F correspond to 50 µg/ml, 5 µg/ml, 0.5 µg/ml, 50 ng/ml, and 5 ng/ml, respectively. FIG. 4d shows a close-up view of a portion of FIG. 4c.

The present invention provides for the following advantages: minimized or no background of the sample holder influences the result; multiple samples can be measured at a time; easy handling and mixing of reagents in the holes possible; easy bubble free filling of holes; low costs for customer and manufacturer; disposable sample holder (slide with holes) as consumable; no contamination of analytical reader, no cleaning necessary; small sample volume; high sensitivity; evaporation of sample volume minimized by additional ingredients of the reagent mix; measurement possible within prolonged time period; sample can be reused if desired; no positioning error of sample; wide range of sample viscosity/composition possible; minimal optical crosstalk from hole to hole; sample remains in hole even if the slide is dropped; droplet geometry to a large degree does not depend on surface tension/viscosity of the sample (sample does not float on surface).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention claimed is:

1. A sample holder for use in an analytical reader, the sample holder comprising:
a substrate with at least one hole for receiving a sample to be analyzed, wherein the at least one hole extends completely through the substrate and is sized such that the sample is held within the at least one hole by means of surface tension of the sample, acting between an inner surface of the substrate defining the hole and the sample,
wherein the substrate comprises a first upper substrate and a second lower substrate that together embed a porous membrane, the holes of the first substrate and the holes of the second substrate, which correspond in arrangement to the holes of the second substrate, together define the at least one hole extending completely through the substrate, with the porous membrane in between,
wherein in that the sample holder further comprises a first membrane attached to a top side of the first upper substrate and a second membrane attached to a bottom side of the second lower substrate to cover the hole on the top and/or bottom side of the sample holder, wherein the sample holder is adapted such that the hole can be filled by immersing the sample holder in a liquid.

2. A sample holder according to claim 1, wherein the porous membrane and/or the first membrane and/or the second membrane are made from a hydrophilic material or a hydrophobic material.

3. A sample holder according to claim 1, wherein the substrate is made from glass, plastic, metal and/or a material having well-defined optical properties so that the sample holder can be used as an optical standard for measurements of the sample within the at least one hole.

4. A sample holder according to claim 1, wherein the at least one hole has a circular shape.

5. A sample holder according to claim 1, wherein an inside surface of the substrate defining the at least hole is a hydrophilic surface.

6. A sample holder according to claim 1, wherein an inside surface of the substrate defining the at least one hole is a hydrophobic surface.

7. A sample holder according to claim 1, wherein the sample holder comprises a plurality of holes, wherein a portion of the plurality of holes has a diameter that is larger than a diameter of another portion of the plurality of holes.

8. A sample holder according to claim 1, wherein the at least one hole has a diameter in the range of 0.1-10 mm.

9. A sample holder according to claim 1, wherein the at least one hole has a diameter in the range of 0.5-3.0 mm.

10. A method of using a sample holder according to claim 1 in an analytical reader, comprising the steps of:
filling the at least one hole of the sample holder with a sample and reagent mixture;
inserting the sample holder in the analytical reader; and
analyzing the sample and reagent mixture in the at least one hole of the sample holder by means of the analytical reader.

11. A method according to claim 10, comprising a further step of adding an anti evaporation agent to the at least one hole for minimizing and/or avoiding evaporation of the sample disposed in the at least one hole of the sample holder, said agent being selected from the group consisting of polyethylenglycol, diethylenglycol, Glycerin, MgCl2, LiCl, CaCl2, Ca(NO3)2, ZnCl2, alcohols, amines and other organic and inorganic compounds.

12. A method according to claim 10, wherein the step of analyzing the sample and reagent mixture in the at least one hole of the sample holder by means of the analytical reader takes into account effects of evaporation by using calibrations and/or models for evaporation.

13. A method according to claim 12, wherein the step of analyzing the sample and reagent mixture in the at least one hole of the sample holder further comprises determining a volume of the sample and reagent mixture in the at least one hole so that the volume can be used to take into account effects of evaporation.

14. The sample holder of claim 1, wherein the analytical reader is an optical reader or an electrochemical reader.

* * * * *